(12) United States Patent
Fitzgerald et al.

(10) Patent No.: US 8,951,232 B2
(45) Date of Patent: Feb. 10, 2015

(54) GASTROSTOMY FEEDING APPARATUS AND METHOD

(75) Inventors: Alan Fitzgerald, Edgeworthstown County (IE); Ciara Deighan, Kinnitty (IE); Paul J. Daly, Tullamore (IE)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 12/478,334

(22) Filed: Jun. 4, 2009

(65) Prior Publication Data

US 2010/0312192 A1 Dec. 9, 2010

(51) Int. Cl.
*A61M 5/32* (2006.01)
*A61J 15/00* (2006.01)
*A61M 39/02* (2006.01)

(52) U.S. Cl.
CPC .......... *A61J 15/0065* (2013.01); *A61J 15/0015* (2013.01); *A61J 15/0026* (2013.01); *A61J 15/0038* (2013.01); *A61M 2039/0223* (2013.01); *A61M 2039/0255* (2013.01); *A61M 2039/0261* (2013.01); *A61M 2039/0276* (2013.01)
USPC ........... 604/175; 604/174; 604/178; 604/270; 604/907; 604/910; 604/912; 604/915

(58) Field of Classification Search
CPC ............. A61M 2039/0255; A61M 2039/0261; A61M 2039/0276; A61M 2039/0223; A61M 39/0247; A61J 15/0015; A61J 15/0026; A61J 15/0034; A61J 15/0038; A61J 15/0042; A61J 15/0053; A61J 15/0061; A61J 15/0065
USPC ......... 604/174, 178, 910, 175, 104, 264, 907, 604/912, 915
See application file for complete search history.

(56) References Cited

U.S. PATENT DOCUMENTS

| 4,596,560 A | | 6/1986 | Simpson | |
| 4,699,616 A | * | 10/1987 | Nowak et al. | 604/180 |
| 4,738,661 A | | 4/1988 | Marut | |
| 4,832,724 A | | 5/1989 | Borrelli et al. | |
| 4,850,953 A | | 7/1989 | Haber et al. | |
| 4,944,732 A | | 7/1990 | Russo | |
| 5,092,850 A | | 3/1992 | Buma | |
| 5,205,803 A | * | 4/1993 | Zemitis | 482/121 |
| 5,273,529 A | * | 12/1993 | Idowu | 604/500 |
| 5,484,420 A | | 1/1996 | Russo | |

(Continued)

FOREIGN PATENT DOCUMENTS

EP 0615740 A1 9/1994
JP 2004215804 A 8/2004

(Continued)

OTHER PUBLICATIONS

Exam Report issued Jan. 30, 2012 in related Canadian Patent Application No. 2705177, 3 pgs.

(Continued)

*Primary Examiner* — Quynh-Nhu H Vu
*Assistant Examiner* — Larry R Wilson (57) ABSTRACT

An apparatus for direct gastric feeding via a gastrostomy tract formed in a patient. The apparatus includes a tube, an internal bolster, an external bolster, and a force-generating device. The force-generating device may include a pair of automatically adjustable spring members on the external bolster. The spring members are responsive to changes in the length of the gastrostomy tract and eliminate the need for periodic adjustment or replacement of the apparatus.

14 Claims, 8 Drawing Sheets

(56) References Cited

U.S. PATENT DOCUMENTS

| | | | |
|---|---|---|---|
| 5,514,133 | A | 5/1996 | Golub et al. |
| 5,601,537 | A | 2/1997 | Frassica |
| 5,637,097 | A | 6/1997 | Yoon |
| 5,727,555 | A | 3/1998 | Chait |
| 5,860,960 | A * | 1/1999 | Quinn .......................... 604/178 |
| 5,910,128 | A | 6/1999 | Quinn |
| 6,030,361 | A * | 2/2000 | Miyashiro ................. 604/96.01 |
| 6,045,536 | A | 4/2000 | Meier et al. |
| 6,231,549 | B1 | 5/2001 | Noecker et al. |
| 6,546,280 | B2 | 4/2003 | Osborne |
| 7,625,361 | B2 | 12/2009 | Suzuki et al. |
| 2002/0042595 | A1* | 4/2002 | Palmer et al. ................ 604/178 |
| 2006/0052752 | A1* | 3/2006 | McMichael ................... 604/175 |
| 2006/0135950 | A1 | 6/2006 | Gomez |
| 2007/0005041 | A1 | 1/2007 | Frassica et al. |
| 2007/0167923 | A1 | 7/2007 | Deal |
| 2009/0287157 | A1 | 11/2009 | Funamura |

FOREIGN PATENT DOCUMENTS

| | | |
|---|---|---|
| JP | 2004261566 A | 9/2004 |
| JP | 2004275624 A1 | 10/2004 |
| JP | 2008126658 | 5/2008 |
| JP | 2009089927 A1 | 4/2009 |

OTHER PUBLICATIONS

European Search Report dated Jun. 22, 2012 from European Application 10005485.7, 8 pages.

Office Action dated Sep. 26, 2013, Chinese Patent Application Serial No. 201010198442.3, 14 pages.

Office Action dated Oct. 20, 2014 in related Chinese Patent Application Serial No. 201010198442.3, 14 pages.

US 2001/0004691 A1, 06/2001, Castaneda et al. (withdrawn)

\* cited by examiner

GASTROSTOMY FEEDING APPARATUS AND METHOD

FIELD OF THE INVENTION

The present invention generally relates to enteral feeding and, more particularly, to apparatus for and methods of gastrostomy feeding.

BACKGROUND OF THE INVENTION

Gastrostomy involves the surgical creation of an opening (gastrostomy tract) through the abdominal wall of a patient into the stomach. A device sometimes referred to as a skin level device or "SLD" is used to line this opening for delivery of nutrition directly into the stomach. An SLD typically includes an internal bolster configured to be positioned inside the stomach, an external bolster configured to be positioned on the skin on the outside of the patient, and a tubular shaft connecting the two bolsters and lining the gastrostomy tract. An SLD of conventional design has a shaft length generally corresponding to the length of the gastrostomy tract of the patient. During feeding sessions a feed tube is attached to the external bolster of the SLD for delivery of nutrients to the stomach. A one-way valve prevents leakage or backflow of gastric contents.

To select a SLD for a patient, a measuring device is used after the gastrostomy tract is created to determine the gastrostomy tract length, and a SLD with a corresponding SLD shaft length is chosen.

A key drawback of conventional SLDs is the need for replacement if the length of the gastrostomy tract changes. For example, if the patient using the SLD gains weight, the length of the gastrostomy tract will increase and an SLD having a longer shaft length is needed. Neglecting to address this issue can result in Buried Bumper Syndrome (BBS), resulting in overgrowth of gastric mucosa over the internal bolster, and/or the internal bolster being forcibly drawn into the gastric wall. Complications arising from BBS can include gastrointestinal bleeding, perforation of the stomach, and even death. Conversely, if the patient loses weight, the length of the gastrostomy tract will decrease and a shorter SLD is required to prevent leakage of gastric contents.

In another example, gastrostomy formation usually leads to inflammation and swelling. A SLD installed at the time of gastrostomy formation will loosen as the inflammation and swelling subsides and the tract length decreases. A step-up 'shim' (e.g., U.S. Pat. No. 6,231,549) may be employed in such cases to effectively reduce the SLD shaft length, but this technique is only useful for a one-time, single-value adjustment and requires manual intervention. Additionally, shims are inoperable in the weight gain scenario described above. Other manual adjustment approaches involve the use of manually adjustable spring clips (e.g., U.S. Patent Application Pub. No. 2006/0052752) or replacing the SLD altogether.

There is a need, therefore, for an improved SLD that avoids the problems and inconveniences associated with conventional SLDs.

SUMMARY OF THE INVENTION

In general, this invention is directed to a gastrostomy feeding apparatus for providing enteral nutrition to a patient via a gastrostomy tract formed in the patient. The apparatus comprises a tube that defines a feeding lumen having an axis and first and second opposite ends. The tube is adapted to be positioned in the gastrostomy tract for delivering enteral nutrition to the patient. The apparatus also includes an internal bolster that is connected to or near the first end of the tube and is adapted to be positioned inside the stomach of the patient, and an external bolster that is connected to or near the second end of the tube and is adapted to be disposed outside the patient. A force-generating device is operable when the internal bolster is positioned against a stomach wall to exert a force in an axial direction with respect to the tube. The axial force exerted by the force-generating device holds the internal bolster in pressure contact with the stomach wall. The length of the force-generating device in the axial direction varies automatically in response to changes in gastrostomy tract length to maintain the pressure contact between the internal bolster and the stomach wall, without manual adjustment or replacement of the apparatus.

This invention is further directed to a method of securing gastrostomy feeding apparatus to a gastrostomy tract of a patient. The method includes providing gastrostomy feeding apparatus that comprises internal and external bolsters connected by a tube. The tube defines a feeding lumen having an axis. The provided apparatus also includes a force-generating device that is extensible and contractible in an axial direction with respect to the tube. The method further involves inserting the internal bolster through the gastrostomy tract of the patient such that the internal bolster is inside the stomach of the patient, the tube is in the gastrostomy tract, and the force-generating device is exerting a force tending to hold the internal bolster in pressure contact with a wall of the stomach. The length of the force-generating device in the axial direction varies automatically in response to a change in the length of the gastrostomy tract, thereby maintaining the pressure contact without manual adjustment of the gastrostomy feeding apparatus.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
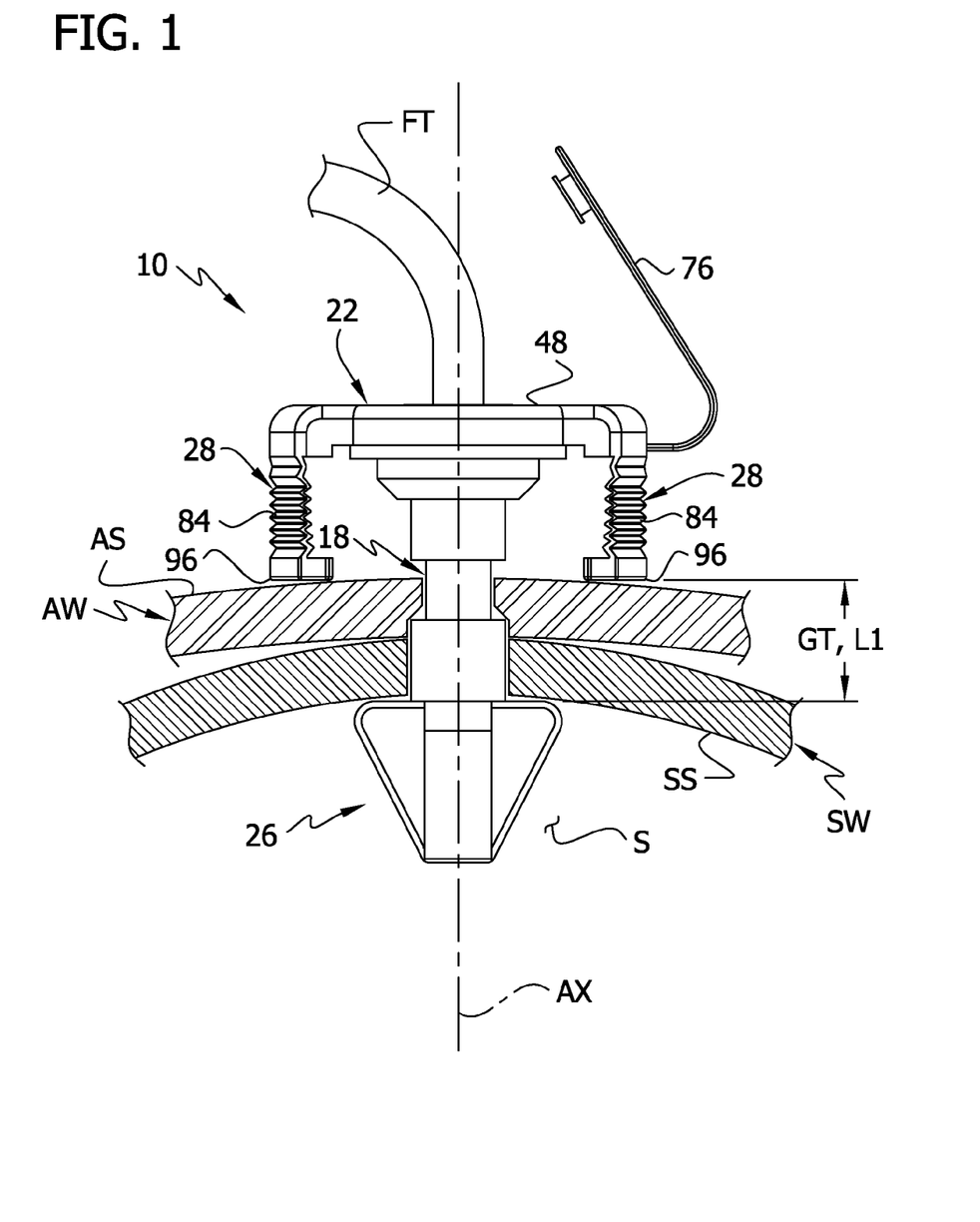
FIG. 1 is a front view showing a skin level device (SLD) of the invention in a gastrostomy tract of a patient.
Figure 2:
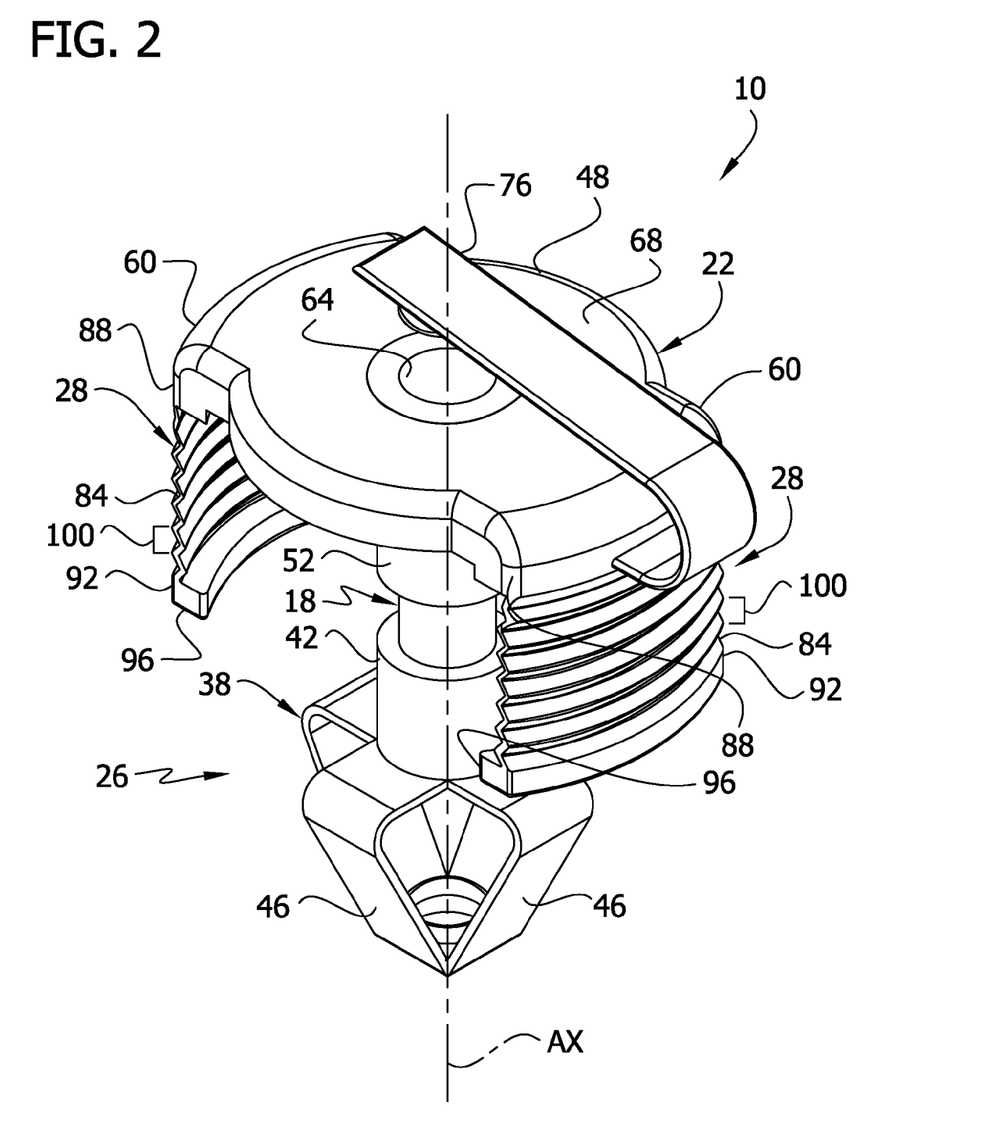
FIG. 2 is a top perspective of the SLD of FIG. 1.

Referring to FIG. 1, an enteral feeding apparatus according to this invention is designated by the reference 10. (This apparatus is hereinafter referred to as a skin level device, or SLD.) The SLD 10 is fitted to a gastrostomy tract GT of a patient for delivering liquid nutrition to the stomach cavity S of the patient. Openings surgically formed in the abdominal wall AW and stomach wall SW of the patient are stitched together to form the gastrostomy tract GT. In general, the SLD 10 comprises a tube 18, an external bolster 22 and an internal bolster 26 which are adapted to be used as shown in FIG. 1. The SLD also includes a force-generating device 28 which is operable when the internal bolster 26 is positioned against a stomach wall surface SS to exert a force in an axial direction with respect to the tube 18 tending to hold the internal bolster 26 in pressure contact with the stomach wall SW. As will described in detail later, the force-generating device 28 has a length in the axial direction which varies automatically in response to a change in the length of the gastrostomy tract GT to maintain the internal bolster 26 in pressure contact with the stomach wall SW without manual adjustment of the SLD 10.

Figure 4:
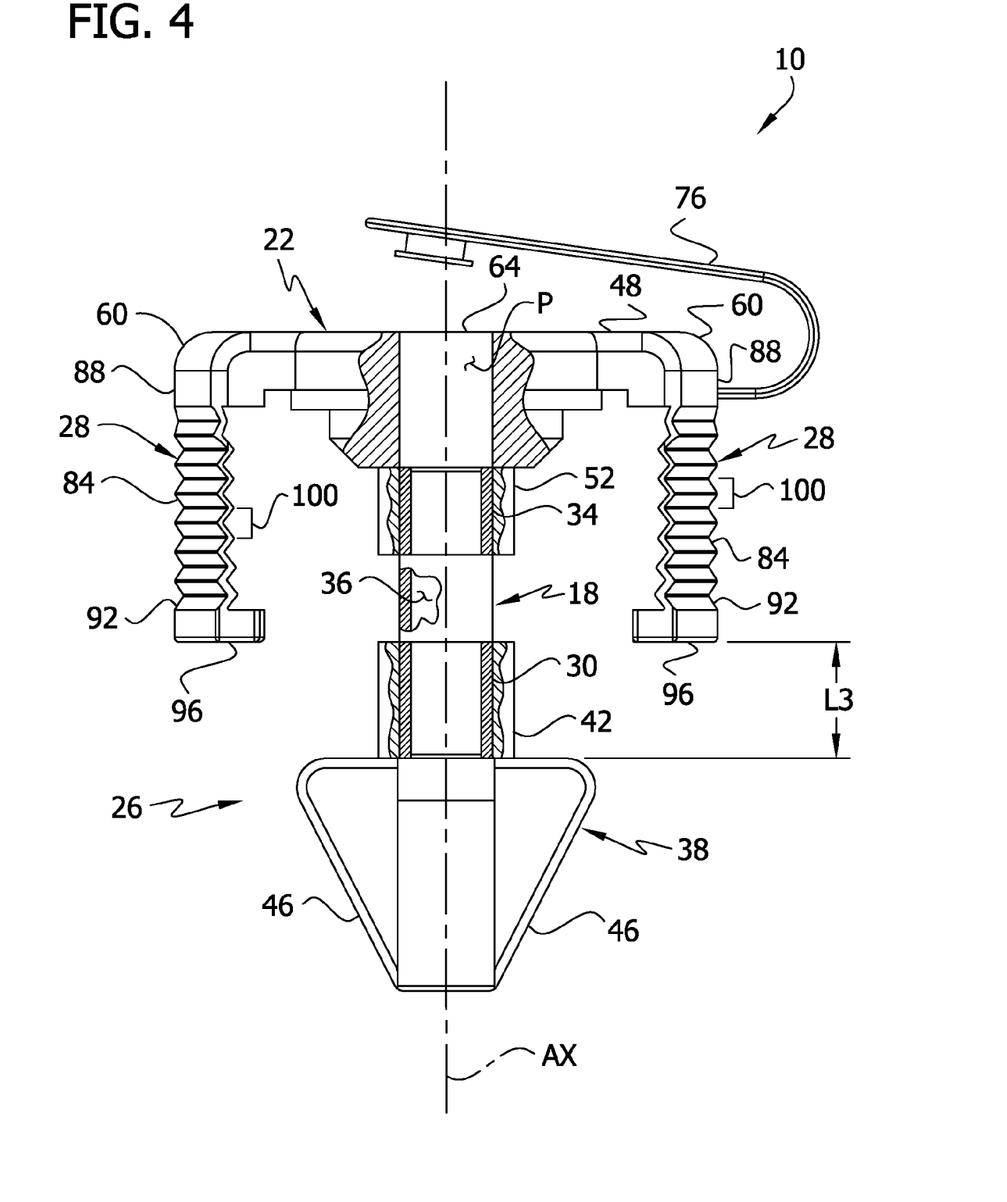
FIG. 4 is a front view of the SLD of FIG. 2, with portions broken away to illustrate details.
Figure 5:
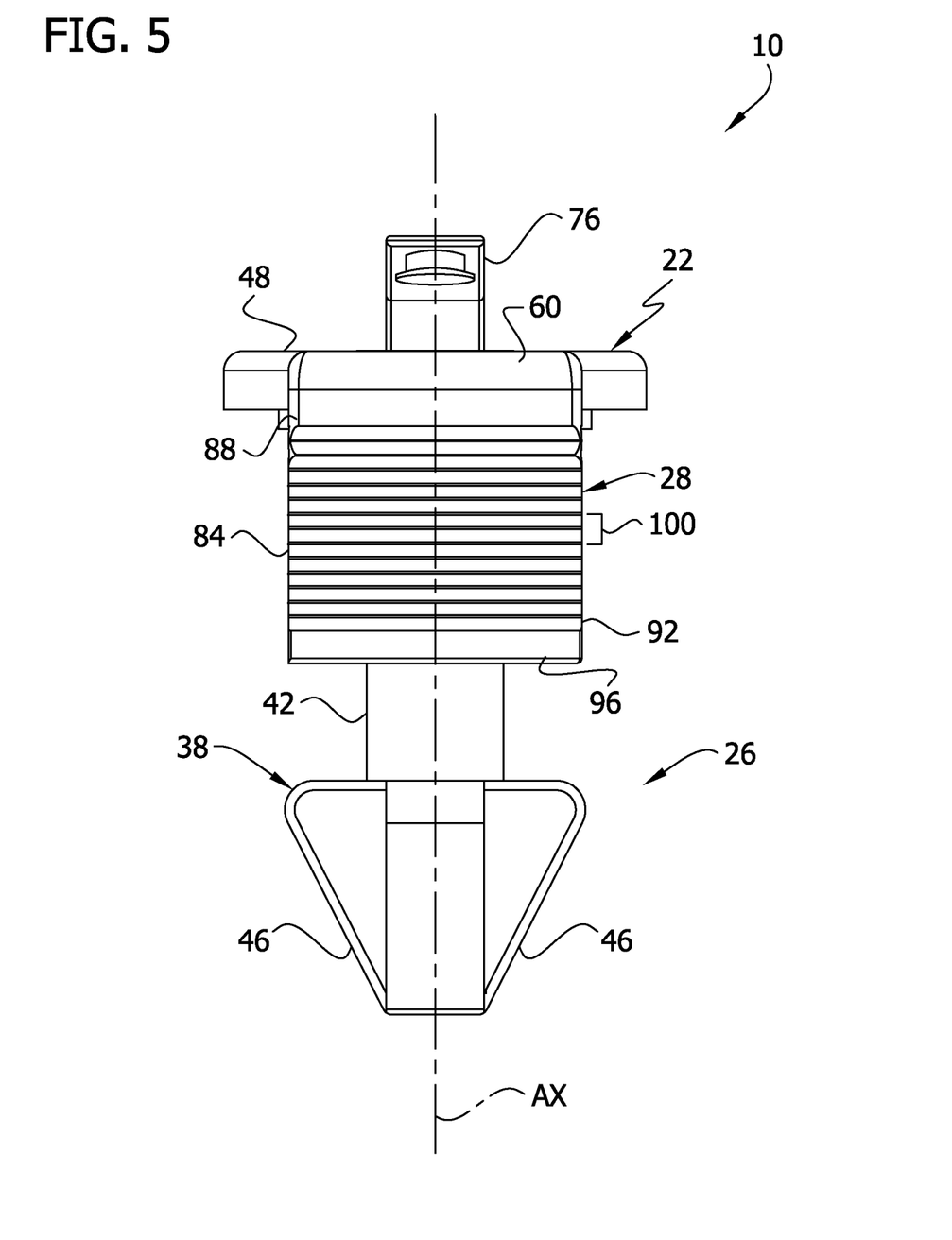
FIG. 5 is a side view of the SLD of FIG. 2.
Figure 6:
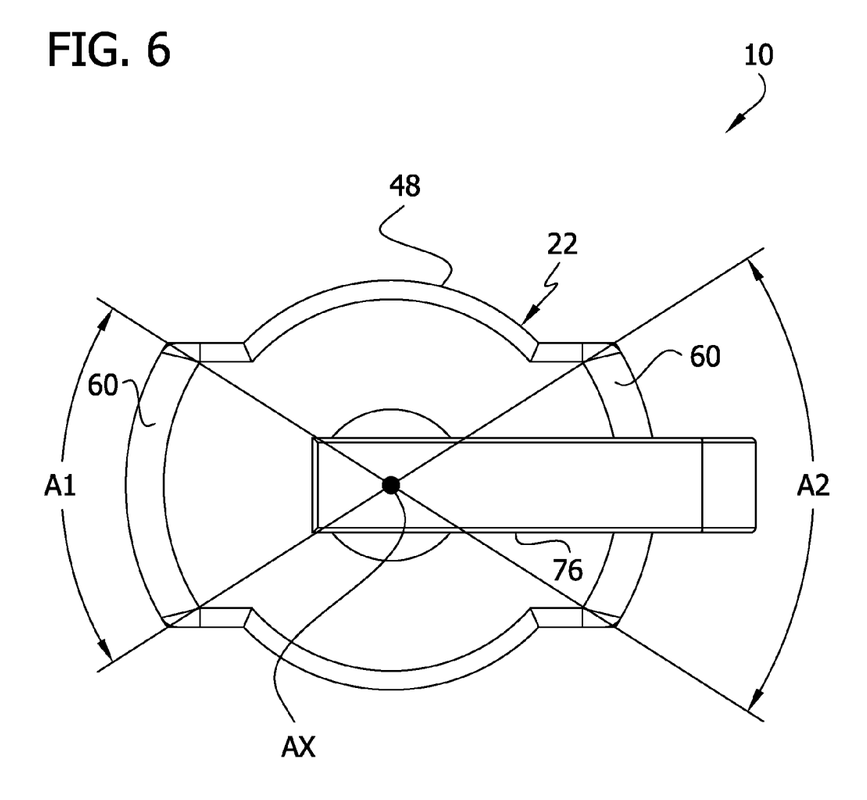
FIG. 6 is a top view of the SLD of FIG. 2.

As shown in FIGS. 1 and 4, the tube 18 of the SLD 10 is disposed in the gastrostomy tract GT. The internal bolster 26 is attached to a first end 30 of the tube 18 and is disposed inside the stomach cavity S. The external bolster 22 is attached to a second end 34 of the tube 18 and is disposed outside the patient on the abdominal wall surface AS. The tube 18 has a generally cylindrical wall that defines a lumen 36 having a longitudinal axis AX. Desirably, the tube 18 has a length and an outer diameter that is at least equal to a length and diameter of the gastrostomy tract GT. Variations of the tube design (e.g., variations in thickness of the cylindrical wall, the shape of the tube, etc.) are within the scope of the invention.

Referring to FIGS. 2-5, the internal bolster 26 comprises a deformable retention structure 38 (best illustrated in FIGS. 4 and 5) and a tubular end section 42 connecting the deformable retention structure 38 to the first end 30 of the tube. The retention structure 38 comprises multiple retaining members 46. The retaining members 46 are movable from a contracted configuration (not shown) in which the structure 38 has a generally uniform radial cross-section comparable to the diameter of the tubular end section 42 for permitting passage of the internal bolster 26 through the gastrostomy tract GT, to an expanded configuration (as shown) in which the structure 38 is wider at its end adjacent the stomach wall SW for contact with the stomach wall surface SS to retain the internal bolster 26 inside the stomach cavity S. Other designs of the internal bolster 26 for enabling insertion and anchoring of the SLD 10 are within the scope of the invention.

As illustrated in FIG. 1-6, the external bolster 22 has a generally circular body 48 centered on the axis AX of the tube 18 and a tubular end section 52 connecting the body 48 to the second end 34 of the tube. Two arms 60 extend laterally out from the body at opposite sides of the body 48. As viewed from above (FIG. 6), the arms 60 have curved outer ends which define arcs of angular measure A1, A2 centered on axis AX. By way of example but not limitation, angles A1 and A2 may be about 60°. Other values are within the scope of the invention. An opening 64 (FIG. 4) extends through the body 48 and communicates with the tubular end section 52. Desirably, the opening 64 is concentric with the axis AX and is sized for receiving either a feeding tube or a feeding tube connector, both generally designated by reference FT in FIG. 1. A closure 76 is tethered to one of the lateral arms 60 for closing the opening 64 between feeding sessions. The closure 76 may be connected to the external bolster 22 in other ways. As best illustrated in FIGS. 1 and 4, the opening 64 and the tubular end sections 42, 52 of the two bolsters 22, 26 are aligned with the lumen 36 of the tube 18 and centered on axis AX to form a passage P for delivering nutrition to the patient from the feeding tube FT. A one way valve (not shown) may be formed anywhere in the passage P to prevent backflow of the liquid nutrients and/or gastric content.

Desirably, the ends 34, 30 of the tube 18 are sealed within the tubular end sections 52, 42 of respective bolsters 22, 26. Other connectors for connecting the bolsters 22, 26 to the tube 18 are within the scope of the invention.

Referring to FIGS. 1-5, the force-generating device 28 is attached to the external bolster 22. The device 28 is a spring device that, in the illustrated embodiment, includes a pair of spring members (each also designated 28) extending from the lateral arms 60 of the external bolster 22 in a direction generally parallel to the axis AX towards the internal bolster 26. Each spring member 28 includes a spring portion 84 that is axially expansible and contractible. The spring member 28 has a first (upper) end 88 that attaches the spring portion 84 to a respective lateral arm 60 and a second (lower) end 92. The connection of the spring portion 84 to the arm 60 is illustrated as an integral (one-piece) connection, but other connections are within the scope of the invention. Each spring member 28 has a foot portion 96 connected to its lower end 92. The foot portion 96 provides an enlarged force-spreading surface for contacting and reacting against the abdominal wall surface AS, thereby improving stability and preventing patient discomfort.

Figure 3:
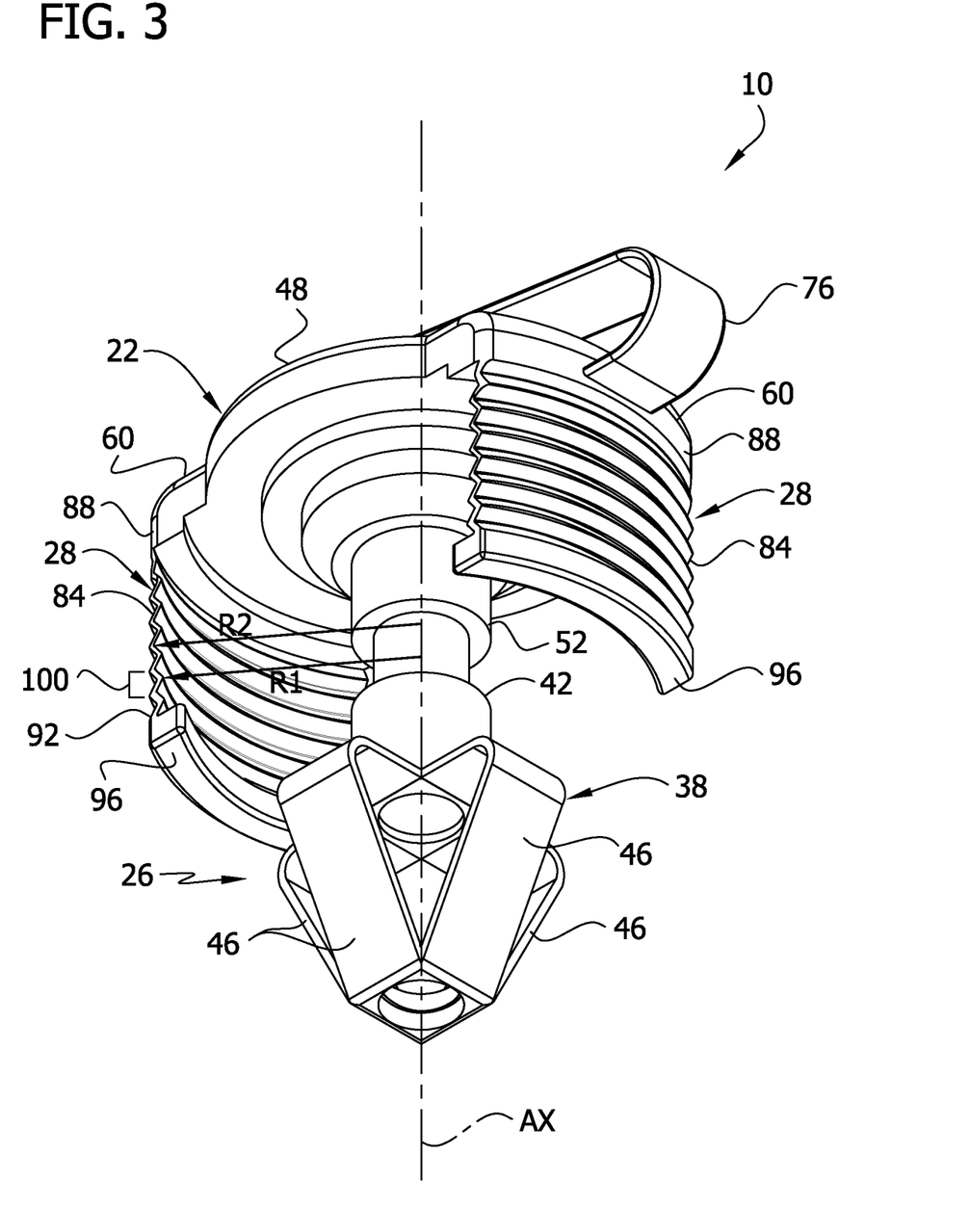
FIG. 3 is a bottom perspective of the SLD of FIG. 2.
Figure 7:
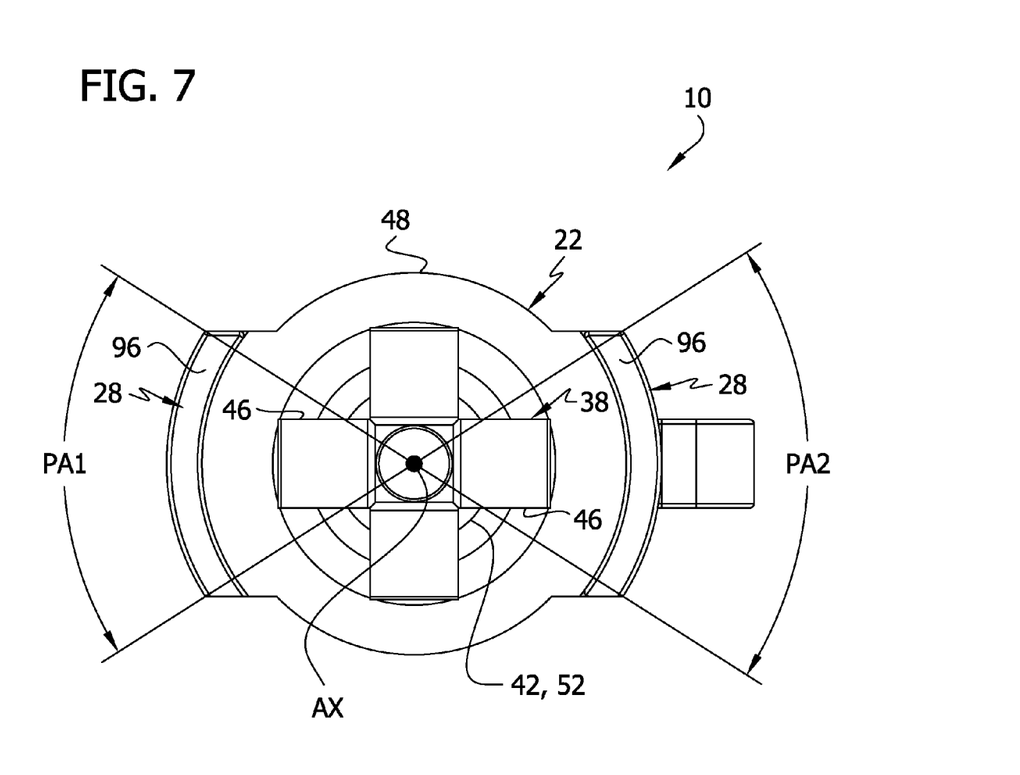
FIG. 7 is a bottom view of the SLD of FIG. 2.

In the illustrated embodiment of FIGS. 3-7, the spring portion 84 of each spring member 28 comprises a plurality of elastic corrugations or pleats 100 which, like the coils of a spring, are resiliently expansible and contractible in an axial direction to produce a force. As best seen in FIGS. 3 and 7, the pleats 100 extend along arcs having inner and outer radii R1, R2 centered on the axis AX. Desirably, the arcs define pleat angles PA1, PA2 that are similar to respective angles A1, A2 of the lateral arms 60. Other values of the radii R1, R2 and pleat angles PA1, PA2 are within the scope of the invention. Other symmetric positions of the spring members 28 about axis AX on the external bolster 22 are within the scope of the invention. Any number of spring members 28, including a single annular spring member, can be used. Desirably, in embodiments where more than one spring member is used, the spring members act independent of one another, that is, they can expand and contract independent of one another to accommodate local variations in stomach wall SW and/or abdominal wall AW thickness.

Returning to FIG. 1, when the various components of the enteral feeding apparatus are positioned as illustrated, the foot portions 96 of the spring members 28 are against the abdominal wall surface AS and the spring portions 84 of the spring members 28 are resiliently contracted to produce an axial force along the axis AX, thereby imparting automatic adjustability to the SLD 10. That is, as the length L1 of the gastrostomy tract GT changes, the length of the spring portions 84 will also change while still providing the force necessary to hold the internal bolster 26 in pressure contact against the stomach wall surface SS. The spring members 28 also serve to distance the body 48 of the external bolster 22 from the abdominal wall surface AS. This feature reduces the amount of bolster area in contact with the skin and helps to prevent abrasion or chaffing.

Again referring to FIG. 1, a method of using the SLD 10 will now be described. The retention structure 38 of the SLD 10 is moved to its contracted position (not shown) and inserted through the gastrostomy tract GT to a position inside the stomach. After entering the stomach, the retention structure 38 resiliently moves to its expanded condition, as shown in FIG. 1, for engagement with the stomach wall SW to resist withdrawal under normal operating conditions. With the retention structure 38 positioned as shown, the tube 18 is disposed substantially in the tract GT, and the external bolster 22 is disposed substantially outside the tract GT on the abdominal wall surface AS. A feeding tube FT is connected to the opening 64 to supply nutrition to the patient.

Figure 8:
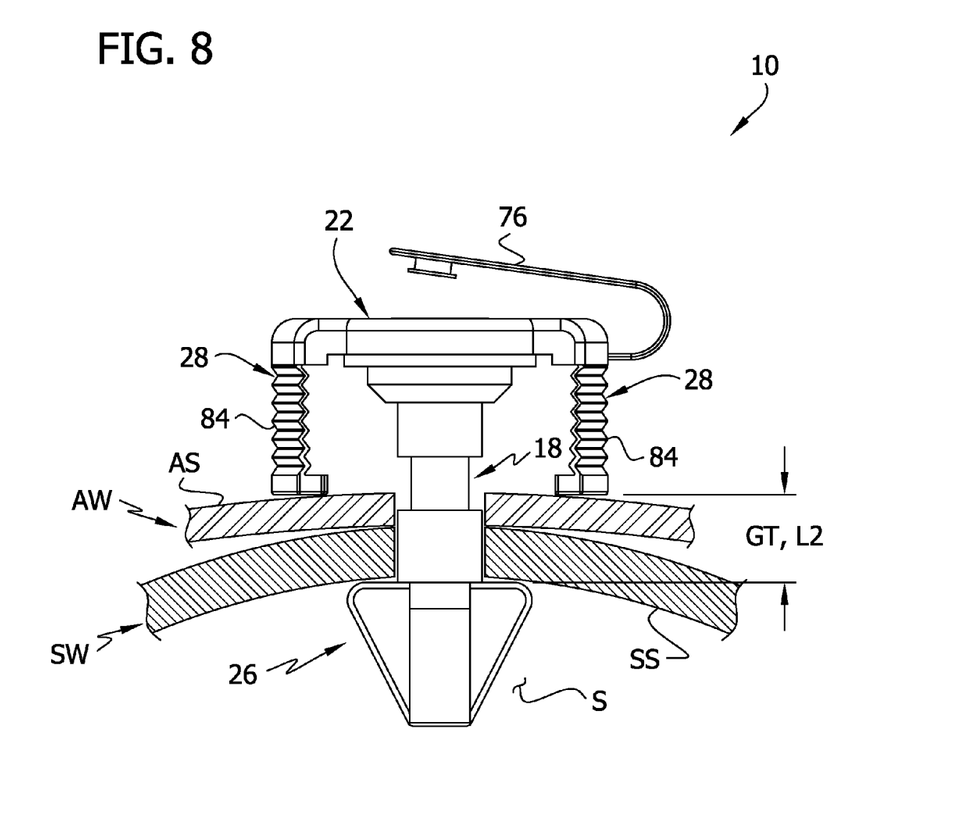
FIG. 8 is a front view of the SLD of FIG. 1 after a reduction in abdominal wall thickness.

With the components positioned as shown in FIG. 1, the spring members 28 are in a contracted condition and exert a force against the abdominal wall surface AS to hold the internal bolster 26 in pressure contact with the stomach wall surface SS. Each spring member 28 of the pair of spring members 28 automatically varies in length independent of the other spring member (as described earlier) and in response to changes in the tract length L1 to maintain the internal bolster 26 in pressure contact without manual intervention. FIGS. 1 and 8 illustrate this automatic adjustability feature. FIG. 1 illustrates the SLD 10 when installed immediately after the tract GT is surgically created. The area surrounding the tract GT is generally inflamed and swollen, which causes the tract GT to have an increased length L1. The spring members 28 contract to a greater extent to accommodate this increased length L1. In FIG. 8, the surgery-induced inflammation and swelling of the abdominal wall AW has subsided, and the tract GT has a reduced length L2. As illustrated, the length of the spring members 28 has increased to accommodate this decrease in length (i.e., L1–L2) of the tract GT. However, the spring members 28 remain contracted to exert the force necessary to maintain the internal bolster 22 in pressure contact with the surface SS. The adjustment is automatic. That is, no manual adjustment or replacement of the SLD 10 is needed. The same automatic adjustment will occur in the event the length of the tract GT changes due to weight gains or losses by the patient, or due to other changes.

The SLD 10 may be part of a gastrostomy kit that also includes placement obturators, bolus feeding sets, continuous feeding sets, and other insertion/removal devices.

The tube 18 and bolsters 22, 26 are formed of generally biocompatible, non-reactive and non-abrasive materials. The tube 18 is preferably rigid, although this is not essential. Further, the retaining members 46 of the internal bolster 26 may be formed of any flexible material, such as silicone or polyurethane. The spring members 28 may be formed of a suitable, elastically deformable material (e.g., PET) that is responsive to forces generated on the SLD 10 during physiological or other changes as described above. Other combination of materials can be used to form various components of the SLD 10 within the scope of the invention.

Having described the invention in detail, it will be apparent that modifications and variations are possible without departing from the scope of the invention defined in the appended claims. For example, in the illustrated embodiment, the force-generating device is a pair of spring members 28 formed on opposite sides of the external bolster 22. However, any number of spring members can be used. For example, a single spring member may be formed near the periphery of the external bolster 22 circumscribing the tubular end section 52. That is, the pleat angle PA1 of the single spring member is 360°. In other embodiments, the tubular end sections 42, 52 may have outer diameters sized to fit inside the tube 18. It is also possible for the entire SLD 10 to be integrally formed. Desirably, various components of the SLD 10 are sized such that the axial distance L3 (FIG. 4) between the foot portions 96 and the upper end of the deformable retention structure 38 is between 0.1 and 0.25 inches when the spring member 28 is in a fully expanded (relaxed) condition.

In view of the above, it will be seen that the several objects of the invention are achieved and other advantageous results attained. A patient that requires direct gastric feeding can use an SLD 10 of this invention without concern about replacement or adjustment due to weight fluctuations, inflammation, etc. The SLD 10 is economical to manufacture and further reduces equipment costs (no shims or replacements are required) and personnel costs (no periodic, manual intervention by health providers is needed).

As various changes could be made in the above constructions and methods without departing from the scope of the invention, it is intended that all matter contained in the above description and shown in the accompanying drawings shall be interpreted as illustrative and not in a limiting sense.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. Gastrostomy feeding apparatus for providing enteral nutrition to a patient via a gastrostomy tract formed in the patient, said apparatus comprising:
   a tube defining a feeding lumen having an axis, said tube having first and second opposite ends and being adapted to be positioned in said gastrostomy tract for delivering enteral nutrition to the patient;
   an internal bolster connected to the tube generally adjacent the first end of the tube, said internal bolster being adapted to be positioned inside the stomach of the patient;
   an external bolster connected to the tube generally adjacent the second end of the tube, said external bolster being adapted to be disposed outside the patient; and
   a force-generating device having a first end attached to the external bolster and a second end free of connection to the internal bolster and spaced from the internal bolster so that when the internal bolster is positioned against a wall of the stomach the external bolster and force-generating device are located entirely outside of the patient, the second end of the force-generating device being operatively engaged with the exterior of the patient when the internal bolster is positioned against the wall of the stomach to exert a force on the patient and in an axial direction with respect to the tube tending to hold the internal bolster in pressure contact with the stomach wall, said force-generating device having a length in said axial direction which varies bidirectionally and automatically in response to a change in the length of the gastrostomy tract to maintain said pressure contact without manual adjustment of the apparatus;
   wherein said force-generating device comprises a spring device comprising at least two spring members connected to said external bolster adjacent a periphery of the bolster and generally on opposite sides of said axis, each of said at least two spring members having a first end connected to the external bolster and an opposite second end adapted to react against the patient for exerting said force.

2. The apparatus of claim 1, wherein the internal and external bolsters have openings therein aligned with said feeding lumen to define a passage for receiving a feeding tube for supplying nutrition to the patient.

3. The apparatus of claim 2, further comprising a closure tethered to the external bolster for closing the opening in the external bolster.

4. The apparatus of claim 1, wherein each of said at least two spring members comprises an axially expansible and contractible spring portion, and a foot portion connected to said spring portion at said second end of the spring member for contact with the patient, the foot portion having an enlarged force spreading surface for contacting and reacting against the patient.

5. The apparatus of claim 1, wherein each of said at least two spring members comprises a plurality of elastic pleats extending along arcs centered on said axis.

6. The apparatus of claim 1, wherein the internal bolster is spaced from the second end of each of said at least two spring members by an axial distance between 0.10-0.25 in. when the spring members are in a fully extended, relaxed condition.

7. The apparatus of claim 1, wherein each spring member of said at least two spring members expands and contracts independent of the other spring member of said at least two spring members.

8. The apparatus of claim 1, wherein the internal bolster comprises a retention structure contractible in a radial direction to permit insertion through the gastrostomy tract and expansible in a radial direction to resist withdrawal from the gastrostomy tract.

9. The apparatus of claim 1, wherein the internal bolster comprises a first end section connected to the first end of the tube and the external bolster comprises a second end section connected to the second end of the tube, said first and second end sections having a first outside diameter and the tube having a second outside diameter less than said first outside diameter.

10. The apparatus of claim 1, in combination with one or more of the following: one or more placement obturators, one or more bolus feeding sets, one or more continuous feeding sets, and one or more insertion/removal devices.

11. The apparatus of claim 1, wherein each of the spring members of said at least two spring members extends from the external bolster along an axis generally parallel to the axis of the lumen towards the internal bolster.

12. A method of securing gastrostomy feeding apparatus to a gastrostomy tract of a patient, said method comprising:
providing gastrostomy feeding apparatus comprising internal and external bolsters connected by a tube defining a feeding lumen having an axis, and a force-generating device extensible and contractible in an axial direction with respect to the tube, said force generating device being attached to the external bolster; and
inserting the internal bolster through the gastrostomy tract of the patient to a position in which: (i) the internal bolster is inside the stomach of the patient; (ii) the tube is in the gastrostomy tract; and (iii) the force-generating device is exerting a force tending to hold the internal bolster in pressure contact with a wall of the stomach, the force generating device is disposed entirely outside the patient, and the force-generating device varying bidirectionally and automatically in length in said axial direction in response to a change in the length of the gastrostomy tract thereby maintaining said pressure contact without manual adjustment of the gastrostomy feeding apparatus;
wherein said force-generating device comprises a spring device comprising at least two spring members connected to said external bolster adjacent a periphery of the bolster and generally on opposite sides of said axis, each of said at least two spring members having a first end connected to the external bolster and an opposite second end adapted to react against the patient for exerting said force.

13. The method of claim 12 further comprising inserting a feeding tube through said feeding lumen, and supplying nutrition to the patient through the feeding tube.

14. The method of claim 12 wherein inserting the internal bolster through the gastrostomy tract includes placing a foot portion of the force generating device against an exterior surface of the patient so that the foot portion bears against the exterior surface of the patient and the force generating device urges the external bolster away from the exterior surface of the patient.

\* \* \* \* \*